US010025087B2

(12) United States Patent
Mori

(10) Patent No.: US 10,025,087 B2
(45) Date of Patent: Jul. 17, 2018

(54) OPTICAL SCANNING OBSERVATION APPARATUS

(71) Applicant: OLYMPUS CORPORATION, Tokyo (JP)

(72) Inventor: Takeshi Mori, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 12 days.

(21) Appl. No.: 15/444,895

(22) Filed: Feb. 28, 2017

(65) Prior Publication Data

US 2017/0168286 A1 Jun. 15, 2017

Related U.S. Application Data

(63) Continuation of application No. PCT/JP2015/004089, filed on Aug. 18, 2015.

(30) Foreign Application Priority Data

Sep. 1, 2014 (JP) .................................. 2014-177164

(51) Int. Cl.
G02B 23/24 (2006.01)
A61B 1/04 (2006.01)
(Continued)

(52) U.S. Cl.
CPC ............ *G02B 23/2469* (2013.01); *A61B 1/04* (2013.01); *A61B 1/07* (2013.01); *G02B 23/2484* (2013.01); *G02B 26/103* (2013.01)

(58) Field of Classification Search
CPC ....... G01V 8/00; E21B 47/102; E21B 47/123; G01D 5/35354; G01D 5/35316;
(Continued)

(56) References Cited

U.S. PATENT DOCUMENTS 9,921,098 B2 * 3/2018 Tanaka .................. G01J 1/0425
9,943,216 B2 * 4/2018 Mikkaichi .......... A61B 1/00089
(Continued)

FOREIGN PATENT DOCUMENTS

JP 2002-360510 A 12/2002
JP 2004-073532 A 3/2004
JP 2013-121455 A 6/2013

OTHER PUBLICATIONS

English translation of International Preliminary Report on Patentability dated Mar. 16, 2017 together with the Written Opinion received in related International Application No. PCT/JP2015/004089.

(Continued)

*Primary Examiner* — Tony Ko
(74) *Attorney, Agent, or Firm* — Scully, Scott, Murphy & Presser, P.C.

(57) ABSTRACT

The optical scanning endoscope apparatus (10) includes: an illumination optical fiber (11) guiding light form lasers (33R, 33G, 33B) and irradiating the light toward an object (100) from an oscillatably-supported tip part of the fiber; an actuator (21) vibratorily driving the tip part of the illumination optical fiber (11); a photodetector (35) detecting light resulting from the object (100) irradiated with the light from the lasers (33R, 33G, 33B) and converting the detected light into an electric signal; a signal processor (37) generating pixel information based on the electric signal output by the photodetector (35); and a light detection controller (31a) controlling a detection property of the photodetector (35) in a period other than an effective detection period.

5 Claims, 9 Drawing Sheets

(51) Int. Cl.
*A61B 1/07* (2006.01)
*G02B 26/10* (2006.01)

(58) Field of Classification Search
CPC ............... G01D 5/35387; G01K 11/32; G01K 11/3206; G01L 9/0076; G01L 9/0077; G02B 6/36
See application file for complete search history.

(56) References Cited

U.S. PATENT DOCUMENTS 9,949,645 B2 * 4/2018 Shida ................... A61B 5/0071
2002/0188176 A1 12/2002 Kuranishi

OTHER PUBLICATIONS

Chinese Office Action dated Sep. 5, 2017 received in 201580044490.8.
International Search Report dated Nov. 17, 2015 issued in PCT/JP2015/004089.
Japanese Office Action dated May 8, 2018 in Japanese Patent Application No. 2014-177164.

* cited by examiner

OPTICAL SCANNING OBSERVATION APPARATUS

CROSS-REFERENCE TO RELATED APPLICATION

The present application is a Continuing Application based on International Application PCT/JP2015/004089 filed on Aug. 18, 2015, which, in turn, claims priority to Japanese Patent Application No. 2014-177164 filed on Sep. 1, 2014, the entire disclosure of these earlier applications being herein incorporated by reference.

TECHNICAL FIELD

The present disclosure relates to an optical scanning observation apparatus which scans light on an object to detect light resulting from the irradiated object, to thereby perform observation.

BACKGROUND ART

Optical scanning observation apparatuses have been conventionally known (see, for example, JP 2013-121455A (PTL 1)). The apparatuses is configured to irradiate laser light emitted from a fiber to form a spot on an observation object, where the tip part of the fiber is caused to vibrate, to thereby spirally scan or raster scan the irradiation position of the laser light. Then, signal light such as transmitted light, reflected light, and fluorescence resulting from the observation object are detected by the light detecting section and converted into an electric signal, which is associated with data on the scanning position at each scan point, to thereby generate image data. An example of such apparatus may include, for example, an optical scanning endoscope apparatus for observing living tissues.

CITATION LIST

Patent Literature

PTL 1: JP2013-121455A

SUMMARY

The disclosed optical scanning observation apparatus, which scans light from a light source onto an object to obtain an image of the object, includes:
  a fiber guiding light form the light source and irradiating the light toward the object from an oscillatably-supported tip part of the fiber;
  an actuator vibratorily driving the tip part of the fiber;
  a light detecting section detecting light resulting from the object irradiated with the light from the light source and converting the detected light into an electric signal;
  a signal processor generating pixel information based on the electric signal output by the light detecting section; and
  a light detection controller controlling a detection property of the light detecting section in a period other than an effective detection period, the effective detection period being an period where the light detecting section detects light obtained from the object and outputs the electric signal, the electric signal output by the light detecting section being used in the signal processor for generating effective pixel information on an image of the object.

The term "effective" pixel information on the object herein refers to image information for use in generating an image of the object to be output for observation by the optical scanning observation apparatus.

Preferably, the detection property of the light detecting section may be a photomultiplication factor. Alternatively, the detection property of the light detecting section may be an offset.

Further, the light detecting section may have a plurality of detection properties, and the light detection controller may sequentially control the plurality of detection properties in a period other than the effective detection period.

The actuator may drive the fiber in a predetermined scanning pattern to repeatedly perform scanning for one frame on the object, and the light detection controller may control the detection property in a period positioned at a boundary between temporally-adjacent frames and outside the effective detection period.

BRIEF DESCRIPTION OF DRAWINGS

In the accompanying drawings:

FIGS. 4A and 4B each illustrate the actuator and the oscillation part of the illumination optical fiber of the optical scanning endoscope apparatus, in which FIG. 4A is a side view thereof, and FIG. 4B is A-A sectional view of FIG. 4A;

DESCRIPTION OF EMBODIMENTS

The optical scanning observation apparatus may use, as light receiving elements of the light detecting section, photodiodes and photomultiplier tubes. Photodetectors output an analog signal corresponding to the received light, but its multiplication factor and offset are known to vary depending on changes in temperature and in use conditions during operation. Thus, in order to obtain stable output, the temperature and offset of the light detecting section need be detected as appropriate to correct the photodetector, based on the detected temperature and offset.

However, no such apparatus capable of correcting the light detecting section as described above has been hitherto proposed. A conceivable method of correcting the temperature may involve providing a temperature sensor for measuring the temperature of the light detecting section to detect the temperature of the light detecting section in operation, to thereby output, to the light detecting section, a signal for correcting the multiplication factor based on the detection result. Here, assuming a case where the temperature sensor detecting the temperature outputs a digital signal, when the temperature is detected simultaneously with the light detecting section detecting signal light and outputting electric signals, digital processing operates in the temperature sensor, which may potentially cause high frequency noise to flow into the output signal of the light detecting section under the influence of the clock. When the output of the light detecting section is affected by high frequency noise, the resulting image data also includes noise, deteriorating the quality of output image.

The offset may be obtained from the photodetector, with the irradiation of laser light being stopped. However, when the output of digital signals by the temperature sensor and the detection and adjustment of the offset from the photodetector temporally overlap, signals from the temperature sensor and from the photodetector interfere with each other, which may result in incorrect setting of the offset. This case also fails to obtain an image with stable quality.

It could therefore be helpful to provide an optical scanning observation apparatus capable of adjusting the detection property of the photodetector without affecting the output of an image of the observation object.

The following describes Embodiments of the disclosed apparatus, with reference to the drawings.

Embodiment 1

Figure 1:
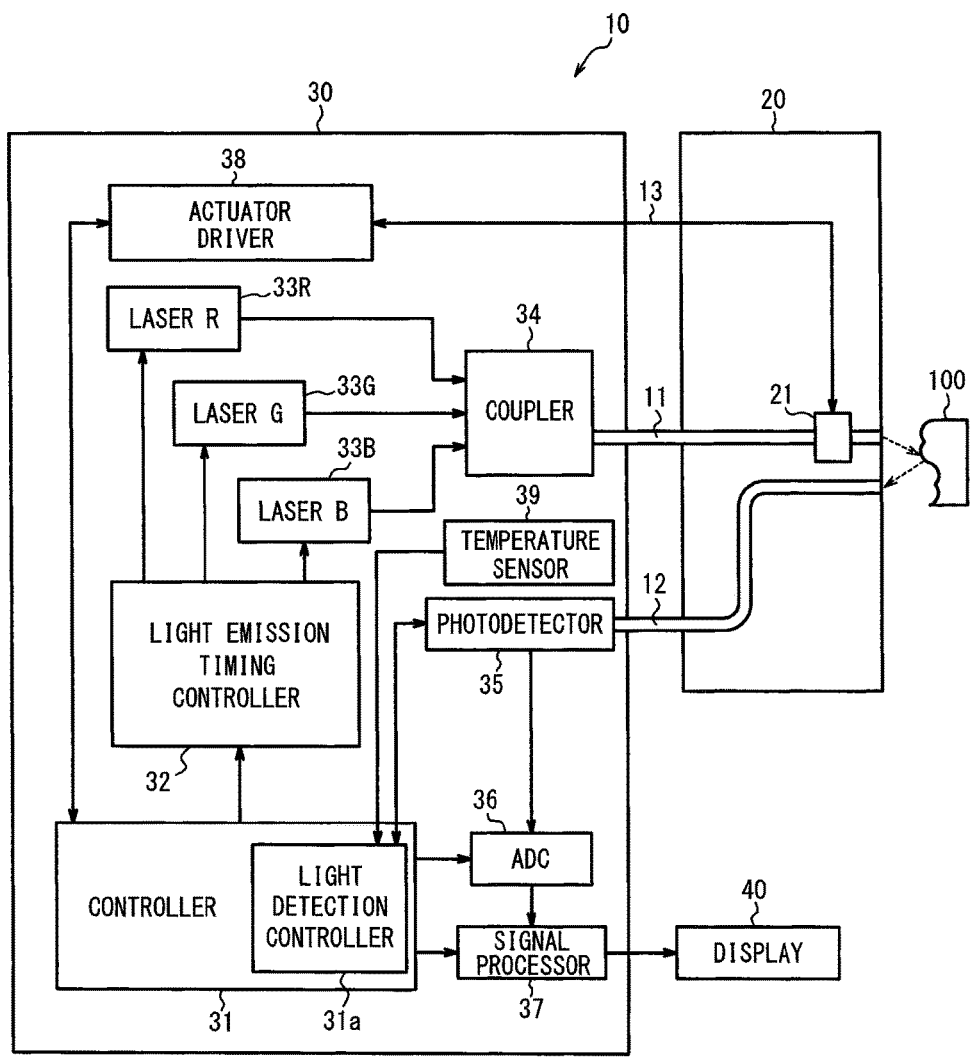
FIG. 1 is a block diagram illustrating a schematic configuration of an optical scanning endoscope apparatus as an example of the disclosed optical scanning observation apparatus according to Embodiment 1.

FIG. 1 is a block diagram illustrating a schematic configuration of an optical scanning endoscope apparatus 10 as an example of the disclosed optical scanning observation apparatus according to Embodiment 1. The optical scanning endoscope apparatus 10 is configured by including: a scope 20, a control device body 30, and a display 40.

The control device body 30 is configured by including: a controller 31 for controlling throughout the optical scanning endoscope apparatus 10; a light emission timing controller 32; lasers 33R, 33G, 33B; and a coupler 34. The light emission timing controller 32 causes, based on the light emission timing instructed by the controller 31, the lasers 33R, 33G, 33B emitting laser lights of three primary colors of red (R), green (G), and blue (B), respectively, to sequentially emit lights at designated timings.

Exemplary lasers that can be used as the lasers 33R, 33G, 33B may include, for example, a diode-pump solid state (DPSS) laser and a laser diode. The paths of laser lights emitted by the lasers 33R, 33G, 33B are coupled, via a coupler 34, to an illumination optical fiber 11 as the same single mode fiber. Needless to say, the light source of the optical scanning endoscope apparatus 10 may use other plurality of light sources, without being limited to the aforementioned configuration. Further, the lasers 33R, 33G, 33B and the coupler 34 may be stored in a separate casing different from the control device body 30, the separate casing being connected to the control device body 30 via a signal line.

The illumination optical fiber 11 is connected through to the tip part of the scope 20, and light incident on the illumination optical fiber 11 from the coupler 34 is guided through to the tip part of the scope 20 to be irradiated as illumination light toward an object 100. Along therewith, an actuator 21 is vibratorily driven, which causes the illumination light emitted from the illumination optical fiber 11 to be spirally scanned on the observation surface of the object 100. The actuator 21 is controlled by the controller 31 via an actuator driver 38 of the control device body 30. Signal light such as reflected light, scattered light, and florescence obtained from the object 100 irradiated with the illumination light is received by the tip ends of a plurality of detection optical fibers 12 constituted of multimode fibers and guided through inside the scope 20 up to the control device body 30.

The control device body 30 further includes: a photodetector 35 (light detecting section); an analog-to-digital converter (ADC) 36; and a signal processor 37, for processing signal light. The photodetector 35 is configured by including light receiving elements such as photodiodes and photomultiplier tubes and a circuit for amplifying and reading out signals, and converts signal light guided through the detection optical fibers 12, into electric signals. Further, the photodetector 35 is configured to be capable of adjusting offset and image magnification of signals, based on external control signals.

The output of the photodetector 35 is converted into a digital signal by the ADC 36 and input to the signal processor 37. The controller 31 calculates information on the scanning position on the scanning path, based on information such as the start time, amplitude, and phase of the vibration voltage applied by an actuator driver 38, and delivers the information thus calculated to the signal processor 37. As a result, the output signal from the photodetector 35 is associated with the scanning position information. Here, the controller 31 may hold in advance, as a table, the scanning position information calculated beforehand. The signal processor 37 synchronizes signals of different wavelengths output in time division from the ADC 36, subjects the signals to necessary image processing such as interpolation processing, emphasis processing, and γ processing, to generate an image of the object 100, and displays the image on the display 40. The signal processor 37 may include, for example, a processor for signal processing, a memory, and a program to be executed by the processor for signal processing.

In the aforementioned processing, the controller 31 synchronously controls the light emission timing controller 32, the photodetector 35, the actuator driver 38, and the signal processor 37.

Figure 2:
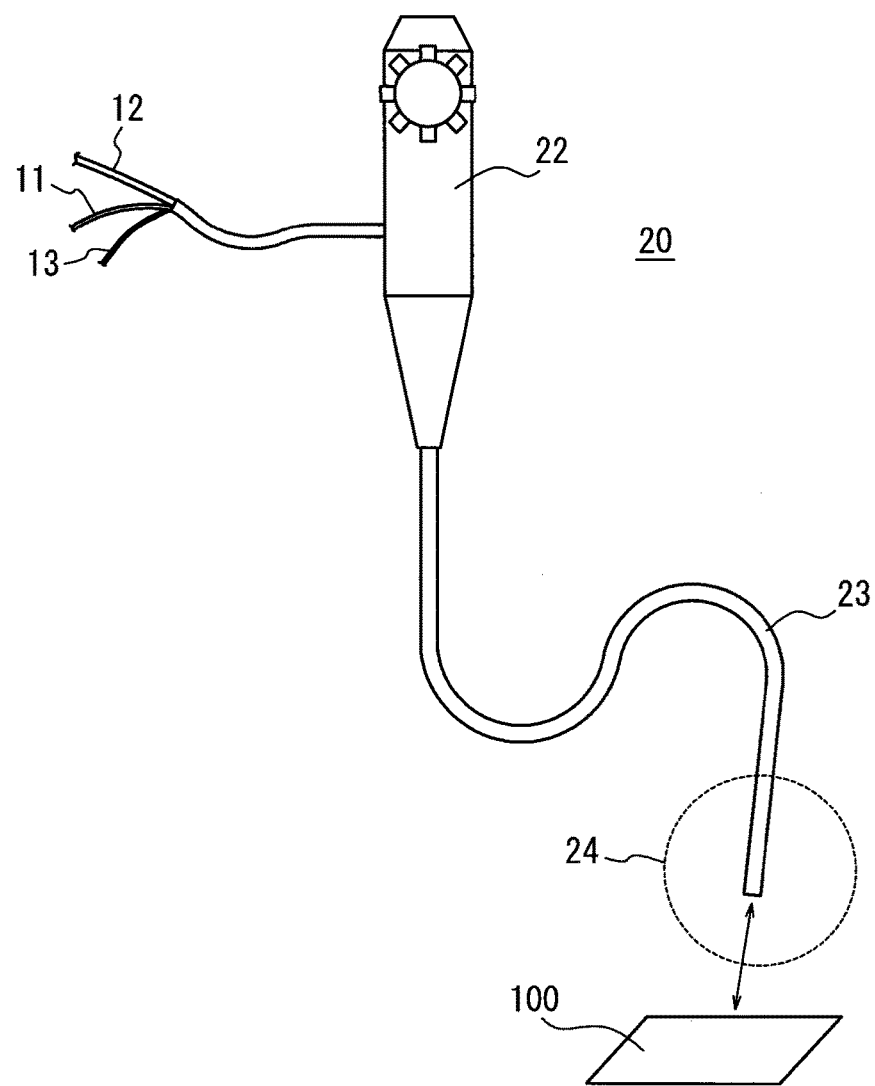
FIG. 2 is an overview schematically illustrating the scope of the optical scanning endoscope apparatus of FIG. 1.

FIG. 2 is an overview schematically illustrating the scope 20. The scope 20 includes an operation portion 22 and an insertion portion 23. The operation portion 22 has the illumination optical fiber 11, the detection optical fibers 12, and the wiring cable 13 from the control device body 30 each connected thereto. The illumination optical fiber 11, the detection optical fibers 12, and the wiring cable 13 each pass through inside the insertion portion 23 to be guided up to the tip part 24 (the portion inside the broken line of FIG. 2) of the insertion portion 23.

Figure 3:
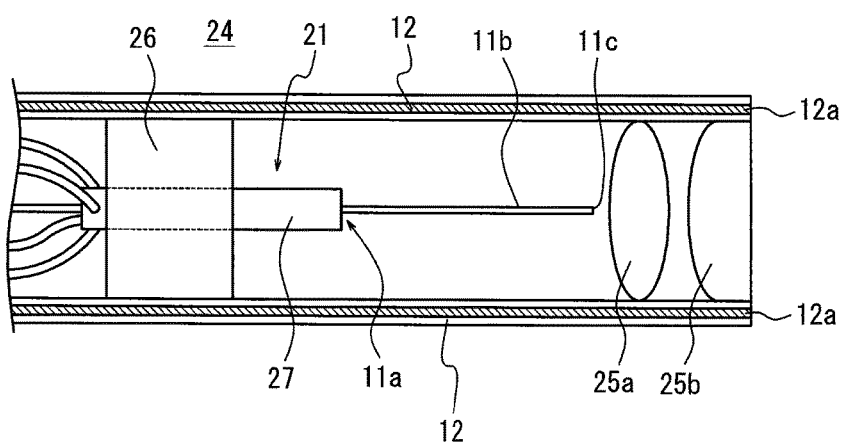
FIG. 3 is a sectional view of the tip part of the scope of FIG. 2.

FIG. 3 is a sectional view of the tip part 24 of the scope 20 of FIG. 2. The tip part 24 is configured by including: the actuator 21; projection lenses 25a, 25b; the illumination optical fiber 11 passing through the center; and the detection optical fibers 12 passing through the outer circumference.

Figure 4A:
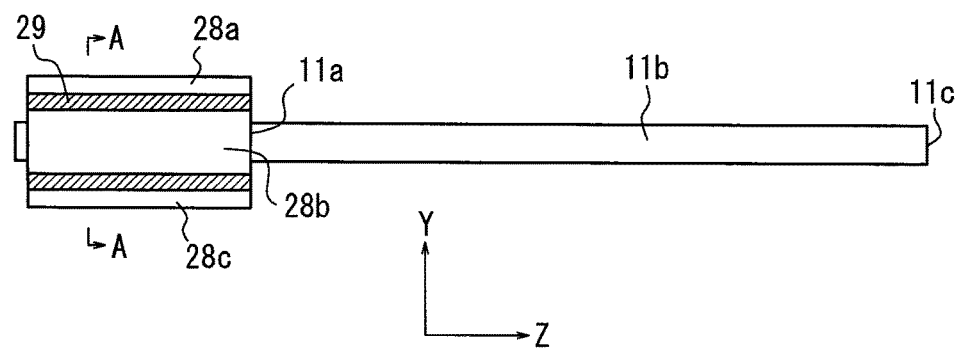
Figure 4B:
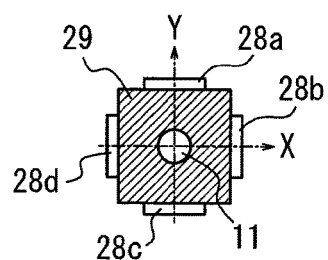

The actuator 21 is configured by including: an actuator tube 27 fixed inside the insertion portion 23 of the scope 20 via an attachment ring 26; and a fiber holding member 29 and piezoelectric elements 28a to 28d disposed inside the actuator tube 27 (see FIGS. 4A and 4B). The illumination optical fiber 11 is supported by the fiber holding member 29 while having an oscillatably-supported oscillation part 11b defined between a fixed end 11a supported by the fiber holding member 29 and the tip part 11c. Meanwhile, the detection optical fibers 12 are arranged so as to pass through the outer periphery of the insertion portion 23 and extends to the tip of the tip part 24 of the insertion portion 23.

Further, the detection optical fibers 12 each include, at the tip part thereof, a detection lens, which is not shown.

Further, the projection lenses 25a, 25b and a detection lens (not shown) are disposed at an extreme tip of the tip part 24. The projection lenses 25a, 25b are arranged such that laser light emitted from the tip part 11c of the illumination optical fiber 11 is irradiated on the object 100 so as to be substantially converged thereon. Thus, the projection lenses 25a, 25b constitute an optical system which irradiates light emitted from the illumination optical fiber 11, toward the object 100. The laser light converged on the object 100 is reflected, scattered, and refracted by the object 100 or obtained as fluorescent, which is taken in as signal light by the detection lens arranged so as to converge and couple the light to the detection optical fibers 12 disposed behind the detection lens. The projection lenses 25a, 25b may include a single lens alone or a plurality of lenses, without being limited to the two-lens configuration.

FIG. 4A illustrates a vibration driving mechanism of the actuator 21 and the oscillation part 11b of the illumination optical fiber 11 of the optical scanning endoscope apparatus 10, and FIG. 4B is A-A sectional view of FIG. 4A. The illumination optical fiber 11 passes through the center of the fiber holding member 29 in a prism shape, so as to be held by the fiber holding member 29. Four side faces of the fiber holding member 29 are each facing +Y-direction, +X-direction and directions opposite thereto. Then, the fiber holding member 29 has the piezoelectric elements 28a, 28c fixed in a pair in the +Y-direction and −Y-direction and the piezoelectric elements 28b, 28d fixed in a pair in the +X-direction and −X-direction.

The piezoelectric elements 28a to 28d are each connected to the wiring cable 13 from the actuator driver 38 of the control device body 30.

Of the piezoelectric elements 28b, 28d disposed opposite to each other in the X-direction across the fiber holding member 29, one expands while the other contracts in a reciprocal manner, to thereby cause deflection in the fiber holding member 29, which may be repeated to generate vibration in the X-direction. Vibration in the Y-direction may similarly be caused. For example, the piezoelectric elements 28b and 28d in the X-direction may employ piezoelectric elements which extend and contract in the same direction with respect to the polarity of the voltage applied, and may always be applied with the same voltage opposite in polarity. Similarly, the piezoelectric elements 28a and 28c in the Y-direction may employ piezoelectric elements which extend and contract in the same direction with respect to the polarity of the voltage applied, and may always be applied with the same voltage opposite in polarity.

The actuator driver 38 controls the piezoelectric elements 28a to 28d such that the tip part 11c of the illumination optical fiber 11 draws a spiral locus. Specifically, the piezoelectric elements 28b, 28d for X-direction driving and the piezoelectric elements 28a, 28c for Y-direction driving may be applied with alternating voltages which vary with time in amplitude from 0 to a maximum value. The alternating voltages are different from one another in phase by 90°, and have frequencies set in the vicinity of the same resonance frequency.

Figure 5:
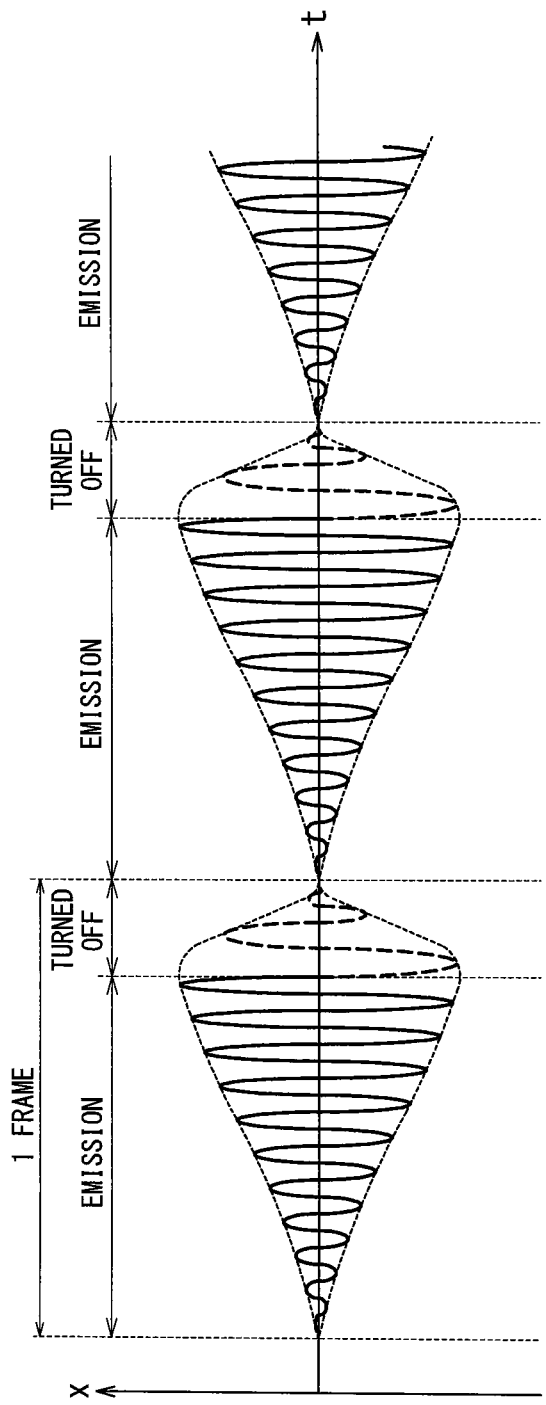
FIG. 5 shows vibration waveforms in the x-direction and y-direction of the illumination optical fiber.

FIG. 5 shows a vibration waveform in the X-direction of the illumination optical fiber 11. As illustrated in FIG. 5, the tip part 11c of the illumination optical fiber 11 vibrates at predetermined intervals in the X-direction as expanding the amplitude from 0 to a predetermined maximum value. When the amplitude reaches the maximum value, the piezoelectric elements 28b, 28d are applied with no voltage or applied with a voltage controlled to reduce the amplitude, which rapidly attenuates the amplitude of the tip part 11c of the illumination optical fiber 11. The amplitude in the Y-direction may similarly be expanded and attenuated. In this manner, the tip part 11c of the illumination optical fiber 11 is drive repeatedly.

Figure 6:
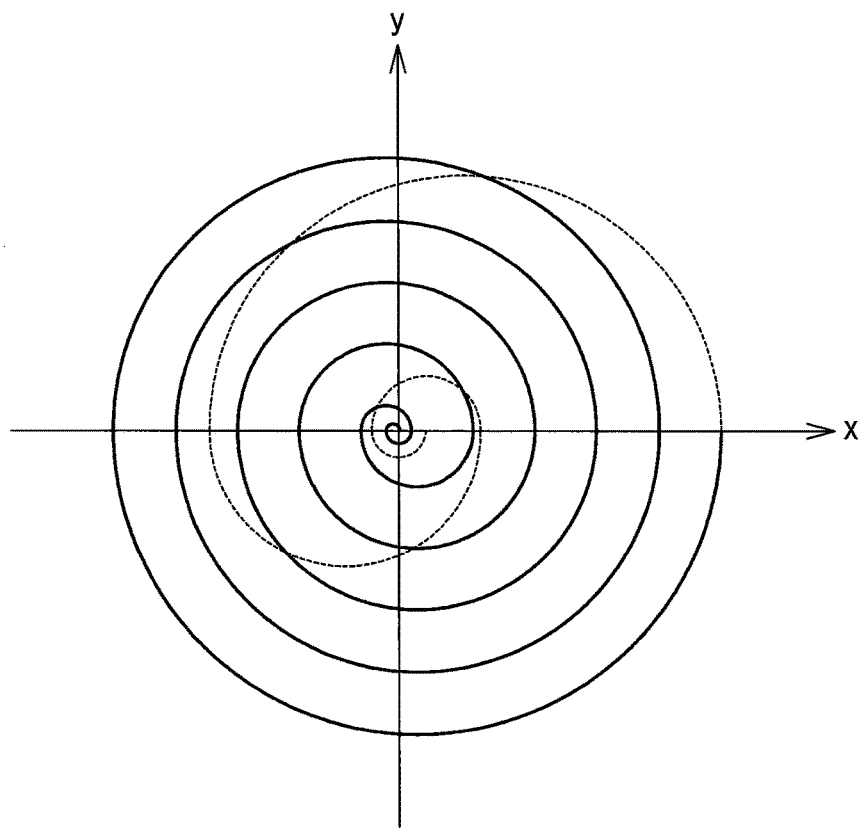
FIG. 6 shows a scanning locus of irradiation light on the observation object.

The controller 31 controls the emission of the lasers 33R, 33G, 33B through the light emission timing controller 32, in synchronous with the driving of the tip part 11c of the illumination optical fiber 11 by the actuator driver 38. The lasers 33R, 33G, 33B are controlled to emit light along the expansion of the amplitude until reaching the maximum value and to turn off during the attenuation thereafter. The tip part 11c of the illumination optical fiber 11 may be controlled as described above, the illumination light emitted from the tip part 11c is scanned on the object 100 as illustrated by the solid line of FIG. 6.

Next, returning to FIG. 1, a method of controlling detection property of the photodetector 35 is described. Here, the detection property refers to a property of the multiplication factor of a signal detected by the photodetector 35. The multiplication factor of the photodetector 35 varies with temperature. Thus, the control device body 30 includes a temperature sensor 39 for measuring the temperature of the photodetector 35. An example of the temperature sensor 39 may include a temperature sensor IC, but other types of temperature sensors such as a thermistor and a thermocouple may also be used. The temperature sensor 39 outputs temperature data as digital signals, to a light detection controller 31a of the controller 31. The light detection controller 31a calculates, based on the temperature data, the multiplication factor for the photodetector 35 for obtaining a preferred output signal level, and generates a signal for controlling the photodetector 35 to have the multiplication factor thus calculated. The light detection controller 31a constitutes part of the controller 31, and may be implemented as a module constituting part of a program implementing the function of the controller 31.

Figure 7:
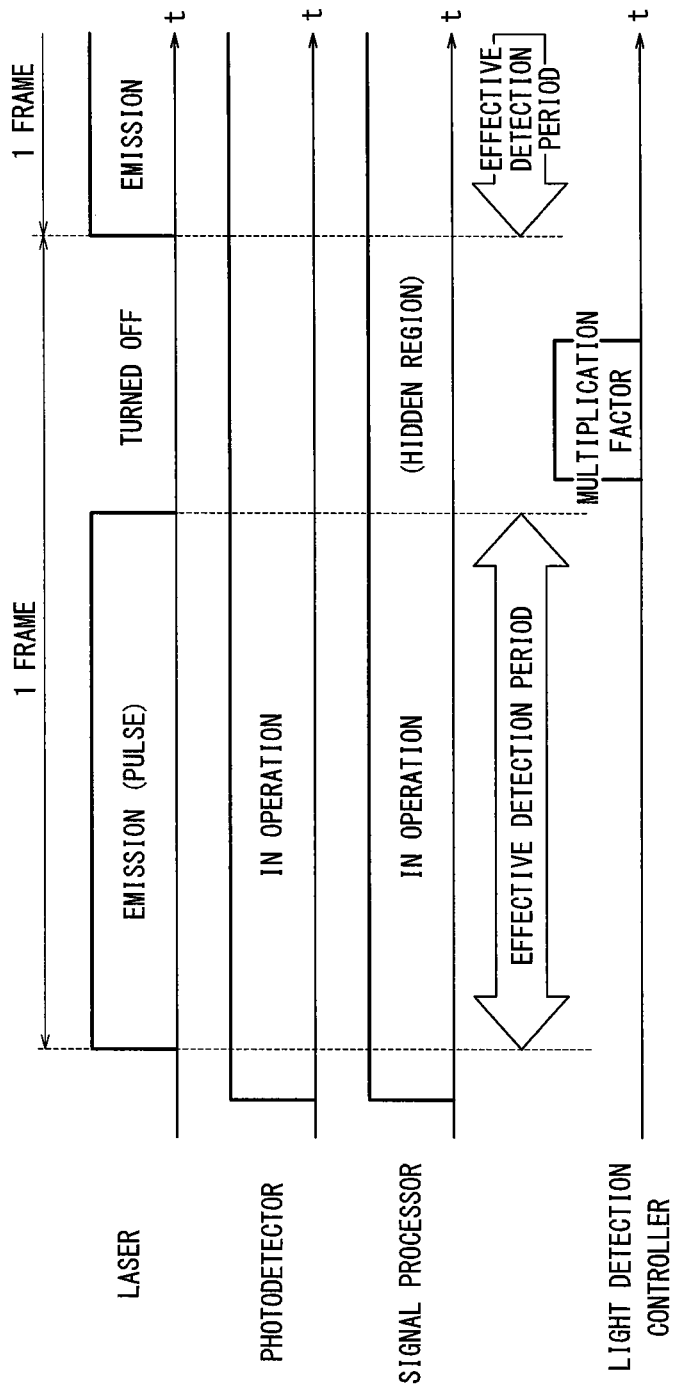
FIG. 7 is a timing chart showing operation states of components of the optical scanning endoscope apparatus according to Embodiment 1.

Next, description is given of the timing of controlling the photodetector 35 by the light detection controller 31a. FIG. 7 is a timing chart showing operation states of the respective components of the optical scanning endoscope apparatus 10 according to Embodiment 1. As explained with reference to FIGS. 5 and 6, the lasers 33R, 33G, 33B are turned on for a period to sequentially repeat continuous emission of light and turned off for another period, while scanning the illumination light for one frame (spiral scan for one cycle) on the object 100. During the period where the lasers 33R, 33G, 33B are emitting light, the photodetector 35 detects reflected light and scattered light obtained from the object irradiated with the illumination light and the signal detected by the ADC 36 is digitized to be processed by the signal processor 37. As described above, defined as an effective detection period is a period where the photodetector 35 is detecting illumination light contributing to image formation of the object and outputting electric signals. Meanwhile, as illustrated in FIG. 7, despite that the lasers 33R, 33G, 33B are turned off, the photodetector 35 and the signal processor 37 are each in the operation state. However, in the turned-off period, no signal light is generated from the object, no effective detection and processing of pixel information is performed.

The light detection controller 31a receives temperature data from the temperature sensor 39 and sets a multiplication factor for the photodetector 35, in a period where the lasers 33R, 33G, 33B are turned off, that is, in a period other than the effective detection period. In a case where the reception of temperature data and the transmission of data on the multiplication factor to be set to the photodetector 35 should fail to be completed within one frame of the period where the lasers 33R, 33G, 33B are turned off, the transmission may be performed across a plurality of frames. In this case, data for giving an instruction of changing the multiplication factor is divided into a plurality of pieces, which are sequentially transmitted in a period other than the effective detection period. The photodetector 35 waits until all the data is received, before changing the multiplication factor.

In this manner, according to Embodiment 1, even when the temperature of the photodetector 35 has changed during the observation by the optical scanning endoscope apparatus 10, such change in temperature can be detected by the temperature sensor 39 and transmitted to the light detection controller 31a. The light detection controller 31a determines the photomultiplication factor for the photodetector 35 and sets the factor to the photodetector 35. Accordingly, undesired variation in the output of the photodetector 35 can be corrected, allowing a stable observation image to be obtained. Further, data for controlling the detection property of the photodetector 35 is generated and set to the photodetector 35 in a period that does not contribute to image formation, the period being outside the effective detection period, to thereby set the detection property of the photodetector 35 without affecting the quality of the image to be generated.

Here, Embodiment 1 illustrates an example where the image data of the object 100 is obtained only in a period where the amplitude of the spiral scan is expanded, with no data obtained in a period where the amplitude is diminished. However, the method of the spiral scan is not limited thereto, and the period of expanding the amplitude and the period of diminishing the amplitude may be set to substantially the same length of time, so that image data for one frame can be obtained for both of the periods of expanding and diminishing the amplitude. In that case, there may be a period where no illumination light for use in generating effective pixel information is irradiated or detected at the boundary between the frames, when scanning the outermost circumference and/or the center of the spiral scan. For example, the outermost circumferential part of the spiral scan may generate a region not to be displayed on the display 40 when the image is displayed. In the vicinity of the center of the spiral scan, where the density of the sampling points is high, sampling may be omitted at some points. Accordingly, laser light may be turned off in a period that does not contribute to image formation, the period being outside the effective detection period, to thereby adjust the multiplication factor of the photodetector 35.

Embodiment 2

Figure 8:
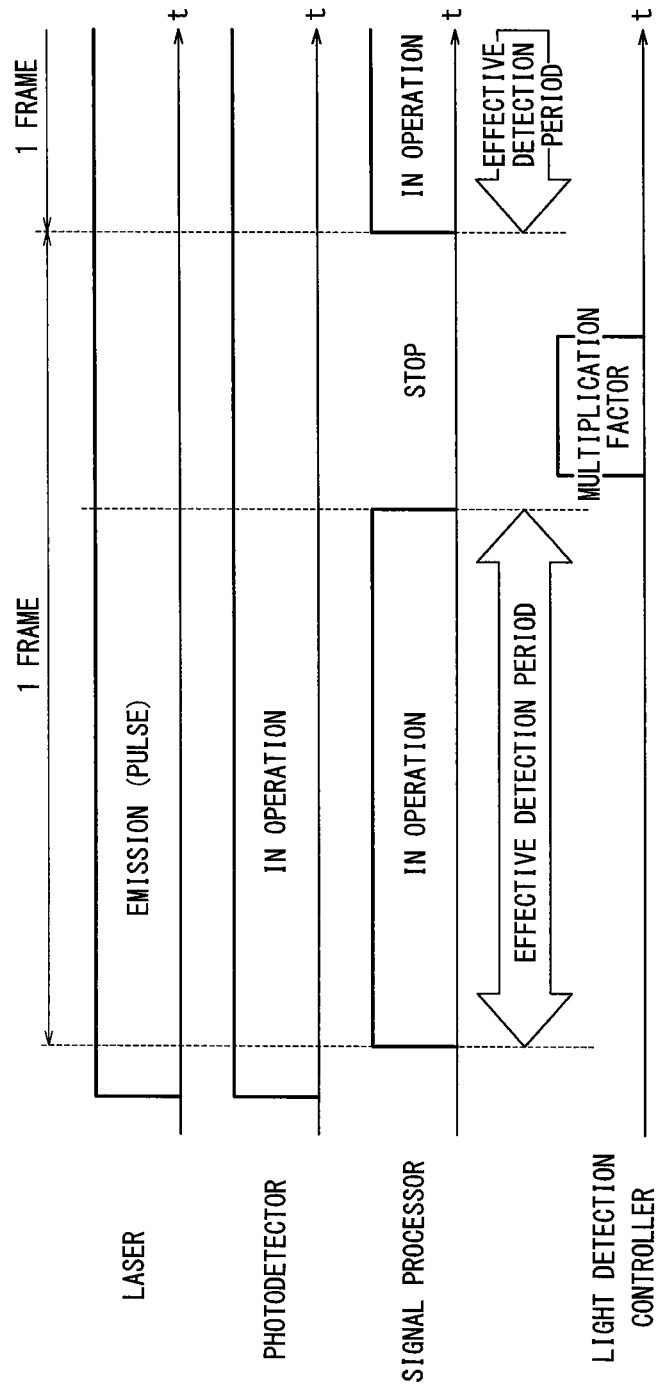
FIG. 8 is a timing chart showing operation states of components of the optical scanning endoscope apparatus according to Embodiment 2.

FIG. 8 is a timing chart showing operation states of components of the optical scanning endoscope apparatus according to Embodiment 2. The optical scanning endoscope apparatus includes the same components as those of the optical scanning endoscope apparatus 10 of Embodiment 1 illustrated in FIG. 1, and thus, the description of each component is omitted.

The optical scanning endoscope apparatus 10 of Embodiment 2 is different from the optical scanning endoscope apparatus 10 of Embodiment 1 in terms of how each component is controlled by the controller 31. In Embodiment 1, the lasers 33R, 33G, 33B are turned off when diminishing the amplitude of the spiral scan. In Embodiment 2, however, the signal processing by the signal processor 37 is stopped, without stopping the sequential pulse emission of the lasers 33R, 33G, 33B. Therefore, in a period where the amplitude of the spiral scan on the object 100 is diminished, light obtained through irradiation of illumination light on the object 100 is only to be detected by the photodetector 35 and then discarded, without being processed by the signal processor 37. Accordingly, the effective detection period for detecting light obtained from an object for use in generating effective pixel information to be used for effective image generation falls under a period where the signal processor 37 is in operation.

The light detection controller 31a receives output of the temperature sensor 39, generates a signal for controlling the multiplication factor of the photodetector 35, and corrects the multiplication factor of the photodetector 35, in a period where the signal processor 37 is stopped. As described above, even in a period where the lasers 33R, 33G, 33B are emitting light, when the signal light detected by the photodetector 35 does not contribute the image formation by the optical scanning endoscope apparatus 10, the detection property of the photodetector 35 can be controlled without giving any influence such as distortion or noise on the image to be generated of the object 100.

In the aforementioned description, the signal processor 37 is stopped in a period of diminishing the amplitude with no pixel data of the spiral scan being obtained. However, the operation of the photodetector 35 may be stopped instead. Alternatively, two or more of the lasers 33R, 33G, 33B, the photodetector 35, and the signal processor 37 may be stopped. The light detection controller 31a is controlled to set the multiplication factor of the photodetector 35 in a period other than the period where the photodetector 35 detects signal light to be used for displaying an effective object image in the later process and outputs the signal light as an electric signal.

Embodiment 3

Figure 9:
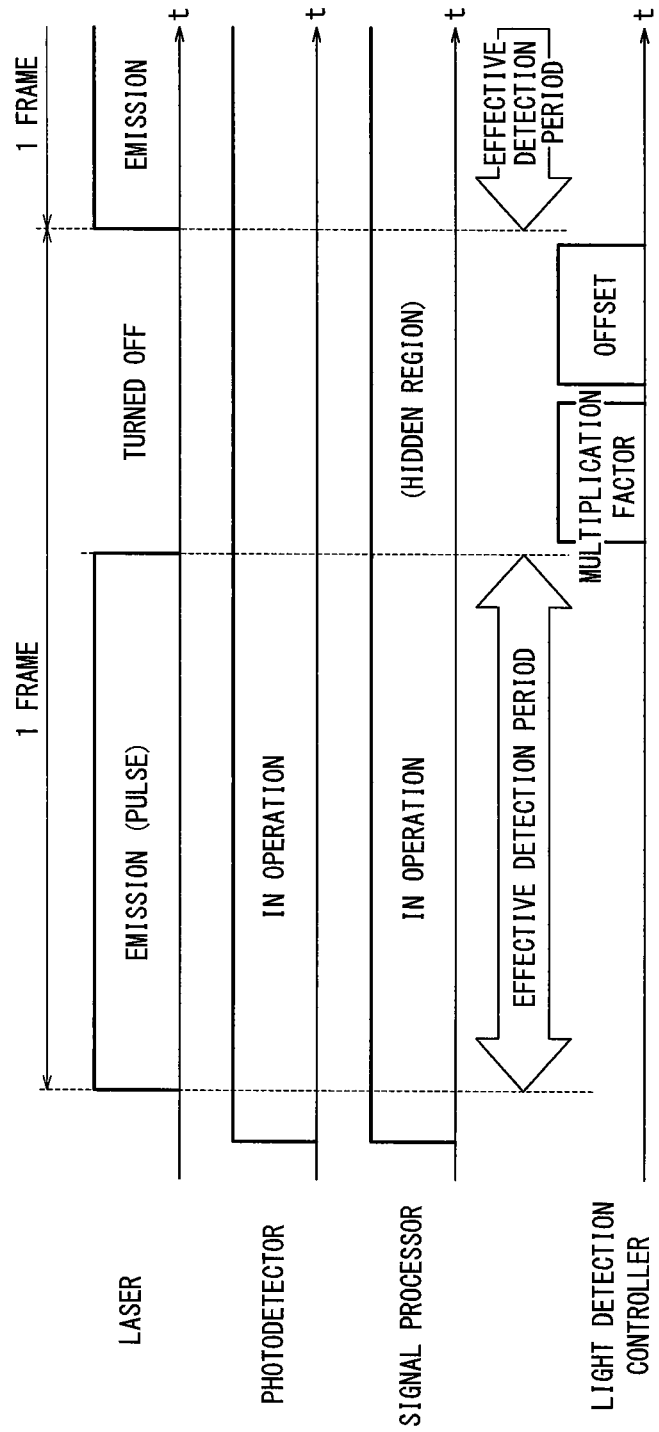
FIG. 9 is a timing chart showing operation states of components of the optical scanning endoscope apparatus according to Embodiment 3.

FIG. 9 is a timing chart showing operation states of the components of the optical scanning endoscope apparatus according to Embodiment 3. Unlike Embodiment 1 which controls only the multiplication factor as the detection property of the photodetector 35, Embodiment 3 additionally controls offset. The optical scanning endoscope apparatus of Embodiment 3 includes the same components as those of the optical scanning endoscope apparatus 10 of Embodiment 1 illustrated in FIG. 1, and thus the description of the apparatus configuration is omitted.

When the lasers 33R, 33G, 33B are turned off along with the reduction of the amplitude during the spiral scan, the light detection controller 31a sequentially executes the control of the multiplication factor of the photodetector 35 based on the temperature detected by the temperature sensor 39 similar to that of Embodiment 1 and the control of offset. To control offset, for example, the photodetector 35 detects an output level from the ADC 36 in a state where the lasers 33R, 33G, 33B are turned off, and determines the output level as the offset and returns the offset to a desired value when the offset is deviated. The multiplication factor and the offset are controlled at predetermined timings that do not temporally overlap each other. Alternatively, data added with a header indicating the type of the data may be sequentially delivered between the light detection controller 31a and the photodetector 35.

The aforementioned configuration allows various kinds of detection properties to be set by the light detection controller 31a to the photodetector 35, which allows further stable pixel signals to be obtained. Further, the multiplication factor and the offset are controlled at temporally separate timings, which can avoid the inter-signal interference to be otherwise generated due to mutual control of two detection properties, to thereby perform stable control. In particular, inter-signal interference between digital signals output from the temperature sensor 39 to the light detection controller 31a and signals for detecting and controlling the offset between the photodetector 35 and the light detection controller 31a can be avoided, which prevents an incorrect value from being set as the offset of the photodetector 35.

The disclosed apparatus is not limited to those of the aforementioned Embodiments, and may be subjected to various alterations and modifications. For example, the method of scanning the object is not limited to spiral scan, which may be Lissajous scan or raster scan. For example, in the case of raster scan, laser irradiation may be stopped when scanning both ends in the lower speed scanning direction, so as to control the detection property of the photodetector by the light detection controller. In this case, the both ends in the low speed scanning direction of the raster scan are not displayed as an image.

Further, in Embodiments above, the detection property of the photodetector is controlled between the frames of the displayed image, but the timing of controlling the detection property of the photodetector is not limited thereto. For example, the detection property of the light detecting section may be controlled during the irradiation of each pulsed light by each laser and reading out of pixel data.

Further, the driving mechanism of the optical scanning observation apparatus may employ an electromagnet to use an electromagnetic force for driving, without being limited to those using piezoelectric elements. The lasers serving as light sources of illumination light may be employ lasers of three wavelengths, which may be continuously oscillated (cw oscillation) simultaneously and multiplexed so as to scan the resulting white illumination light on the object, instead of having the lasers to sequentially cause pulse emission at separate timings. In the case of scanning white illumination light, the signal light may be separated for each wavelength in the former stage of the light detecting section and detected by different photodetectors, to thereby obtain signals for the respective wavelengths.

REFERENCE SIGNS LIST 10 optical scanning endoscope apparatus
11 illumination optical fiber
11a fixed end
11b oscillation part
11c tip part
12 detection optical fiber
13 wiring cable
20 scope
21 actuator
22 operation portion
23 insertion portion
24 tip part
25a, 25b projection lens
26 attachment ring
27 actuator tube
28a to 28d piezoelectric element
29 fiber holding member
30 control device body
31 controller
31a light detection controller
32 light emission timing controller
33R, 33G, 33B laser
34 coupler
35 photodetector
36 ADC
37 signal processor
38 actuator driver
40 display

The invention claimed is:

1. An optical scanning observation apparatus which scans light from a light source onto an object to obtain an image of the object, the apparatus comprising:
a fiber guiding light form the light source and irradiating the light toward the object from an oscillatably-supported tip part of the fiber;
an actuator vibratorily driving the tip part of the fiber;
a light detecting section detecting light resulting from the object irradiated with the light from the light source and converting the detected light into an electric signal;
a signal processor generating pixel information based on the electric signal output by the light detecting section; and
a light detection controller controlling a detection property of the light detecting section in a period other than an effective detection period, the effective detection period being an period where the light detecting section detects light obtained from the object and outputs the electric signal, the electric signal output by the light detecting section being used in the signal processor for generating effective pixel information on an image of the object.

2. The optical scanning observation apparatus according to claim 1, wherein the detection property of the light detecting section is a photomultiplication factor.

3. The optical scanning observation apparatus according to claim 1, wherein the detection property of the light detecting section is an offset.

4. The optical scanning observation apparatus according to claim 1, wherein the light detecting section has a plurality of detection properties, and the light detection controller sequentially controls the plurality of detection properties in a period other than the effective detection period.

5. The optical scanning observation apparatus according to claims 1, wherein the actuator drives the fiber in a predetermined scanning pattern to repeatedly perform scanning for one frame on the object, and the light detection controller controls the detection property in a period positioned at a boundary between temporally-adjacent frames and outside the effective detection period.

\* \* \* \* \*